United States Patent [19]

Hoover et al.

[11] 4,067,976
[45] Jan. 10, 1978

[54] ALPHA-AMINO-ALPHA-(UREIDOPHENYL-)ACETAMIDOCEPHALOSPORINS AND THEIR PHARMACEUTICAL COMPOSITIONS

[75] Inventors: John Russel Eugene Hoover, Glenside, Pa.; Jerry Arnold Weisbach, Cherry Hill, N.J.

[73] Assignee: SmithKline Corporation, Philadelphia, Pa.

[21] Appl. No.: 728,580

[22] Filed: Oct. 1, 1976

Related U.S. Application Data

[62] Division of Ser. No. 357,763, May 7, 1973, Pat. No. 4,007,173.

[51] Int. Cl.² .................. A61K 31/545; C07D 501/22; C07D 501/32
[52] U.S. Cl. .................................... 424/246; 544/30

[58] Field of Search ...................... 260/243 C; 424/246

[56] References Cited

U.S. PATENT DOCUMENTS

| 3,341,531 | 9/1967 | Lewis et al. ...................... 260/243 C |
| 3,464,985 | 9/1969 | Holdrege .......................... 260/243 C |
| 3,573,295 | 3/1971 | Johnson et al. .................. 260/243 C |

*Primary Examiner*—Nicholas S. Rizzo
*Assistant Examiner*—David E. Wheeler
*Attorney, Agent, or Firm*—Stuart R. Suter; William H. Edgerton

[57] ABSTRACT

Cephalosporins with a α-amino-(ureidophenyl-)acetamido substituent at position 7 are prepared by acylation of a 7-aminocephalosporin with a derivative of α-amino-p(or m)-ureidophenylacetic acid. These compounds are antibacterial agents.

15 Claims, No Drawings

ALPHA-AMINO-ALPHA-(UREIDOPHENYL-)ACETAMIDOCEPHALOSPORINS AND THEIR PHARMACEUTICAL COMPOSITIONS

This is a division of application Ser. No. 357,763 filed May 7, 1973, now U.S. Pat. No. 4,067,173.

This invention relates to new cephalosporin compounds with improved properties. In particular, the new compounds have an heterocyclicthiomethyl group at position 3 and a ureidophenylglycyl substituent at position 7 of the cephem nucleus. These compounds have antibacterial activity when administered either orally or parenterally.

Since the discovery of the cephalosporins as a new group of antibacterials, a wide variety of semi-synthetic analogs has been prepared. Although many derivatives have been found that display a high degree of activity when administered parenterally, the discovery of cephalosporins that have oral activity has presented a difficult problem. Cephaloglycine, U.S. Pat. No. 3,560,489; cephalexin, U.S. Pat. No. 3,507,861; and cephradine, U.S. Pat. No. 3,485,819 are the only compounds that have commercial use in this area. We have now discovered a new series of cephalosporins that have oral activity.

The compounds of this invention are defined by the following formula:

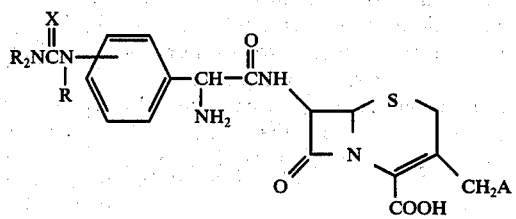

wherein:
The $R_2NCXNR$ group is at the para or meta position;
R is hydrogen or lower alkyl of 1–4 carbon atoms;
X is oxygen or sulfur;
A is hydrogen, acetoxy, methylthio, methoxy, azido, or SHet; and
Het is a 5 or 6-membered heterocyclic ring containing carbon and 1–4 atoms selected from the group consisting of N, O, and S, unsubstituted or substituted with one or two substituents selected from the group consisting of $C_1$–$C_6$ alkyl, $C_1$–$C_6$ alkoxy, allyloxy, oxide, carboxamido, carboxyl, carbalkoxy of $C_1$–$C_6$, halogen, mercapto, methylthio, trifluoromethyl, hydroxy, amino, alkylamino and dialkylamino, each undefined alkyl having 1–6 carbon atoms.

Het includes N-oxide derivatives of the heterocyclic systems named where such derivative is possible, for example, pyridyl-N-oxide.

Preferred compounds are those where Het is tetrazolyl, triazolyl, thiadiazolyl, oxadiazolyl, diazolyl, pyridyl, primidyl and pyrazinyl.

Also preferred are compounds where R is hydrogen. Particularly preferred compounds are those where Het and R are as preferred above and X is oxygen.

Due to the presence of the amino and carboxylic acid groups, the compounds of this invention can exist as the zwitterion or an acid or base salt. These salts are prepared by standard methods using a wide variety of nontoxic pharmaceutically acceptable acids and bases that are known in the art.

The asymmetric carbon in the ureidophenylglycine aide chain gives rise to optical isomers, of which the diastereomers having the D-configuration in the sidechain are preferred; however, those having the L-configuration and the diastereomeric mixtures derived from acylations using racemic side chain acids are within the scope of the invention.

The compounds of this invention are prepared by acylation of the appropriate 7-aminocephalosporin nucleus with the appropriate ureidophenylglycine. The carboxylic acid group is activated by any of the standard methods such as mixed anhydride, acid chloride, or activated ester. In addition, a coupling reagent, for example dicyclohexylcarbodiimide, can be used provided that the carboxyl group on the cephem nucleus is protected with an easily removable protecting group. The amino group of the glycine moiety must also be protected during the acylation. Examples of protecting groups known in the art are t-butoxycarbonyl, trichloroethoxycarbonyl, benzyloxycarbonyl, the methyl acetoacetate adduct, or similar groups commonly used in peptide synthesis.

Alternatively, the compounds where A is SHet may be prepared by acylating 7-aminocephalosporanic acid with the N-protected ureidophenylglycine and then displacing the acetoxy group with the desired heterocyclicthiol. Removal of the protecting group gives the product compounds of this invention.

The starting materials are known, prepared by known methods, or described herein. Ureidophenylglycines, both the meta and para compounds, are prepared from p-aminophenylglycine and m-aminophenylglycine (U.S. Pat. No. 3,479,339) by first protecting the glycine amino group and then reacting the phenyl amino group with cyanate ion. The thioureidophenylglycines are similarly prepared by using t-butyl isothiocyanate and hydrolyzing the t-butyl group. The monoalklureido compounds are prepared by substituting an alkyl isocyanate for the cyanate ion or by reacting N-alkylaminophenylglycine with cyanate ion after first protectig the glycine amino group. The dialkylureido derivatives are prepared by substituting dialkylcarbamyl chloride for the cyanate ion. The 7-amino-3-heterocyclicthiomethyl-3-cephem-4-carboxylic acids are prepared by displacing the acetoxy group of 7-aminocephalosporanic acid (7-ACA) with a heterocyclicthiol by the method disclosed in U.S. Pat. No. 3,516,997.

The compounds have antibacterial activity against both Gram-positive and Gram-negative organisms and are therefore useful for the treatment or prevention of bacterial infections. These compounds are particularly useful since the antibacterial activity in animals is observed when they are administered either parenterally or orally. Minimum inhibitory concentrations (MIC) were determined using the standard tube dilution method. 3-Methyl-7-(α-amino-p-ureidophenylacetamido)-3-cephem-4-carboxylic acid (93916) had MIC's ranging from 3.1 to greater than 200 μg/ml when tested against a variety of bacteria. In addition, 3-(5-methyl-1,3,4-thiadiazol-2-ylthiomethyl)-7-(α-amino-p-ureidophenylacetamido)-3-cephem-4-carboxylic acid (88062) had MIC's ranging from 0.4 to greater than 200 μg/ml. The in vivo activity of these compounds was demonstrated by administering the compounds to mice infected with E. coli and Kleb. pneumonia. The results from both oral and subcutaneous administration are reported in Table 1 as $ED_{50}$ in mg/kg along with those of a standard, cephalexin.

TABLE 1

| Compound * | E. coli | | K. pneumo. | |
| --- | --- | --- | --- | --- |
| | sc | po | sc | po |
| 93916 | 37 | 45 | 22 | 19 |
| 35236 | 7.5 | 25 | 11 | 45 |
| 88026 | 2 | 4 | 3 | 2 |
| 66036 | <3 | 5 | 5 | 5 |
| 56136 | 4 | 7 | 5 | 7 |
| 66136 | <3,2 | 9,6 | <3,2 | 10,3 |
| Cephalexin | 15 | 25 | 25 | 16 |

*See Table 2 for structures

TABLE 2

| Compound | R | A |
| --- | --- | --- |
| 93916 | p-ureido | hydrogen |
| 35236 | p-ureido | acetoxy |
| 88026 | p-ureido | 5-methyl-1,3,4-thiadiazol-2-ylthio |
| 66036 | p-ureido | 1-methyltetrazol-5-ylthio |
| 56136 | m-ureido | 5-methyl-1,3,4-thiadiazol-2-ylthio |
| 66136 | m-ureido | 1-methyltetrazol-5-ylthio |

The compounds are formulated in the same manner as other cephalosporins. They are administered parenterally as sterile aqueous solutions or orally as tablets, capsules, or suspensions. The amount given varies with age, size, and condition of the subject as well as the severity of the infection.

The following examples are presented to illustrate the invention but are not to be viewed as limiting the scope thereof.

EXAMPLE 1

α-t-Butoxycarbonylamino-p-ureidophenylacetic acid

A mixture of p-aminophenylglycine (27.73 g, 0.17 mol), t-butyl-2,4,5-trichlorophenylcarbonate (46.94 g, 0.23 mol), triethylamine (67.25 ml), t-butyl alcohol (165 ml), and water (110 ml) were stirred and heated at 62° for 2 hours. The alcohol was removed in vacuo at 40° and the residue was diluted with water (190 ml), acidified to pH 3 with 40% $H_3PO_4$ and then extracted with ethyl acetate. The combined extracts were washed with 5% $NaHCO_3$ (3 × 175 ml). The aqueous washings were cooled, acidified to pH 3.0 with 40% $H_3PO_4$, and extracted with ethyl acetate. The dried extracts were evaporated to give the N-t-butoxycarbonyl derivative. Additional product was obtained from an emulsion which formed during the extraction. Total yield was 14.5 g.

The above product (8.18 g, 0.03 mol) was reacted with potassium cyanate (3.3 g, 0.04 mol) in acetic acid (8 ml) and water (105 ml) for 8.5 hours at 55°. The reaction solution was cooled, acidified to pH 1 with 3 N HCl and extracted with ethyl acetate. The dried extracts were evaporated in vacuo to give the title compound: mp 137°–139° (dec).

EXAMPLE 2

3-(5-Methyl-1,3,4-thiadiazol-2-ylthiomethyl)-7-(α-amino-p-uriedophenylacetamido)-3-cephem-4-carboxylic acid The product from Example 1 (3.1 g, 0.01 mol) was dissolved in dry tetrahydrofuran (60 ml) and then triethylamine (1.4 ml) and N-methylmorpholine (2 drops) were added. The resulting solution was cooled to −15° and i-butyl chloroformate (1.3 ml, 0.01 mol) was added. After stirring the reaction for 25 minutes at −10°, a cold solution of 7-amino-3-(5-methyl-1,3,4-thiadiazol-2-ylthiomethyl)-3-cephem-4-carboxylic acid (3.44 g, 0.01 mol) in a mixture of 50% aqueous tetrahydrofuran (80 ml) and triethylamine (1.4 ml) was added. Additional triethylamine was added to adjust the reaction solution to pH 6.8–7. The reaction was stirred at room temperature for 3 hours followed by evaporation of the THF. The aqueous solution was extracted with ethyl acetate, which was discarded, and then adjusted to pH 1 with 3N HCl while stirring with ethyl acetate. Phases were separated and the aqueous phase was reextracted with ethyl acetate. The combined extracts were dried and evaporated to the solid N-protected derivative. This product was purified by dissolving in methanol (50 ml) and then diluting with ether (500 ml).

The N-protected derivative (1.12 g) was added to ice cold trifluoroacetic acid (12 ml) and was stirred without further cooling for 7 minutes. The solvent was removed in vacuo and ether was added to the residue. The solid salt was collected, stirred with water, and filtered from the insoluble material. The aqueous solution was treated with basic ion exchange resin (Amberlite IR-45) until pH 4.7 was obtained and then filtered. The title product was obtained by lyophization of the water solution: mp <300°.

EXAMPLE 3

3-Methyl-7-(α-amino-p-ureidophenylacetamido)-3-cephem-4-carboxylic acid

To a solution of the product from Example 1 (4.8 g, 0.0154 mol) and t-butyl 7-amino-3-desacetoxycephalorporanate (4.12 g, 0.016 mol) in dry tetrahydrofuran (100 ml) was added dicyclohexylcarbodiimide (3.5 g, 0.017 mol). The reaction is stirred at room temperature for 2 hours and then the solid urea filtered off. The filtrate was evaporated to a foam which was triturated with ether: ethyl acetate to give 4.5 g of the t-butyl ester of the title product.

The ester (4.4 g) was stirred with ice cold trifluoroacetic acid (45 ml) with further cooling in ice for 1 hour. The reaction was evaporated, ether was added to the residue, and the salt was collected. The salt was dissolved in water and treated with basic ion-exchange resin (Amberlite IR-45) until pH 4.75 was obtained. After filtration, the aqueous solution was lyophilized to give the desired product: mp >300°.

EXAMPLE 4

3-(1-Methyltetrazol-5-ylthiomethyl)-7-(α-amino-p-ureidophenylacetamido)-3-cephem-4-carboxylic acid When 7-amino-3-(1-methyltetrazol-5-ylthiomethyl)-3-cephem-4-carboxylic acid (3.28 g, 0.01 mol) was acylated with the product of Example 1 (3.1 g, 0.01 mol) according to the procedure of Example 2, the title compound was obtained: mp >300°.

EXAMPLE 5

3-(1,2,3-Triazol-4-ylthiomethyl)-7-(α-amino-p-ureidophenylacetamido)-3-cephem-4-carboxylic acid To a stirred solution of α-t-butoxycarbonylamino-p-ureidophenylacetic acid (10.1 g, 0.0375 mol) in dry THF (150 ml) is added triethylamine (5.2 ml, 0.0375 mol). The mixture is cooled to −10° and then isobutyl chloroformate (4.92 ml, 0.0375 mol) is added dropwise over a 10 minute period. The reaction mixture is stirred at −10° for 70 minutes and then a cold solution of 7-ACA (10.1 g, 0.0375 mol) in 50% aqueous THF (140 ml) and triethylamine (6.75 ml, 0.0487 mol) is added over a 15 minute period. The reaction is stirred at −5° to 0° for 1 hour and at room temperature for two hours. The organic solvents are evaporated and water (150 ml) is added to the aqueous residue. The solution is extracted with ethyl acetate and the aqueous phase is separated, covered with fresh ethyl acetate, acidified to pH 2.8, and filtered. The phases are separated and the acidic solution reextracted with ethyl acetate. The extracts of the acidified aqueous solution are combined, dried, and evaporated to give the N-t-butoxycarbonyl derivative of 7-(α-amino-p-ureidophenylacetamido)-cephalosporanic acid.

A mixture of the above product (2.77 g, 4.93 mmol) in pH 6.4 phosphate buffer (30 ml) is treated with NaHCO$_3$ (1.085 g, 12.33 mmol) and then 4-mercapto-1,2,3-triazole (0.748 g, 7.4 mmol). The solution is warmed to 70° and stirred at 70° ± 3° for 2.75 hours. The solution is cooled, filtered, and acidified to pH 2.5 producing a residue. The solvents are decanted and the residue is washed with water. The product is dissolved in ethyl acetate, washed with water, dried, and evaporated to the N-protected product.

The protected product is stirred at 0° to 5° with a 9:1 trifluoroacetic acid: anisole solution for 70 minutes. The solvents are evaporated and the residue is poured with rapid stirring into ether (350 ml). The trifluoroacetate salt of the product is collected, washed with ether, dissolved in water, and then stirred with basic ion-exchange resin. The aqeuous solution is lypholized to give the product.

EXAMPLE 6

When an equimolar amount of the following 7-amino-3-heterocyclicthiomethyl-3-cephem-4-carboxylic acids are substituted for 7-amino-3-(5-methyl-1,3,4-thiadiazol-2-ylthiomethyl)-3-cephem-4-carboxylic acid in the procedure of Example 2, the corresponding 7-(α-amino-p-ureidophenyl acetamido)-3-heterocyclicthiomethyl-3-cephem-4-carboxylic acid is formed.

7-Amino-3-(tetrazol-5-ylthiomethyl)-3-cephem-4-carboxylic acid
7-Amino-3-(1,3,4-thiadiazol-2-ylthiomethyl)-3-cephem-4-carboxylic acid
7-Amino-3-(5-trifluoromethyl-1,3,4-thiadiazol-2-ylthiomethyl)-3-cephem-4-carboxylic acid
7-Amino-3-(5-ethyl-1,3,4-thiadiazol-2-ylthiomethyl)-3-cephem-4-carboxylic acid
7-Amino-3-(5-n-butyl-1,3,4-thiadiazol-2-ylthiomethyl)-3-cephem-4-carboxylic acid
7-Amino-3-(5-dimethylamino-1,3,4-thiadiazol-2-ylthiomethyl)-3-cephem-4-carboxylic acid
7-Amino-3-(5-mercapto-1,3,4-thiadiazol-2-ylthiomethyl)-3-cephem-4-carboxylic acid
7-Amino-3-(3-methylthio-1,2,4-thiadiazol-5-ylthiomethyl)-3-cephem-4-carboxylic acid
7-Amino-3-(3-methyl-1,2,4-thiadiazol-5-ylthiomethyl)-3-cephem-4-carboxylic acid
7-Amino-3-(1,2,4-triazol-3-ylthiomethyl)-3-cephem-4-carboxylic acid
7-Amino-3-(5-methyl-1,2,4-triazol-3-ylthiomethyl)-3-cephem-4-carboxylic acid
7-Amino-3-(4-methyl-1,2,4-triazol-3-ylthiomethyl)-3-cephem-4-carboxylic acid
7-Amino-3-(4,5-dimethyl-1,2,4-triazol-3-ylthiomethyl)-3-cephem-4-carboxylic acid
7-Amino-3-(2,5-dimethyl-1,2,4-triazol-3-ylthiomethyl)-3-cephem-4-carboxylic acid
7-Amino-3-(4-methyl-5-trifluoromethyl-1,2,4-triazol-3-ylthiomethyl)-3-cephem-4-carboxylic acid
7-Amino-3-(5-ethyl-1,2,4-triazol-3-ylthiomethyl)-3-cephem-4-carboxylic acid
7-Amino-3-(4-ethyl-1,2,4-triazol-3-ylthiomethyl)-3-cephem-4-carboxylic acid
7-Amino-3-(1-methyl-1,2,4-triazol-5-ylthiomethyl)-3-cephem-4-carboxylic acid
7-Amino-3-(1-methyl-1,2,4-triazol-3-ylthiomethyl)-3-cephem-4-carboxylic acid
7-Amino-3-(1-ethyl-1,2,4-triazol-5-ylthiomethyl)-3-cephem-4-carboxylic acid
7-Amino-3-(1-ethyl-1,2,4-triazol-3-ylthiomethyl)-3-cephem-4-carboxylic acid
7-Amino-3-(4-allyl-1,2,4-triazol-3-ylthiomethyl)-3-cephem-4-carboxylic acid
7-Amino-3-(5-methoxymethyl-1,2,4-triazol-3-ylthiomethyl)-3-cephem-4-carboxylic acid
7-Amino-3-(5-cyclopropyl-1,2,4-triazol-3-ylthiomethyl)-3-cephem-4-carboxylic acid
7-Amino-3-(5-bromo-1,2,4-triazol-3-ylthiomethyl)-3-cephem-4-carboxylic acid
7-Amino-3-(5-hydroxy-4-methyl-1,2,4-triazol-3-ylthiomethyl)-3-cephem-4-carboxylic acid
7-Amino-3-(5-hydroxy-4-ethyl-1,2,4-triazol-3-ylthiomethyl)-3-cephem-4-carboxylic acid
7-Amino-3-(5-hydroxy-1,2,4-triazol-3-ylthiomethyl)-3-cephem-4-carboxylic acid
7-Amino-3-(1-methyl-1,2,3-triazol-5-ylthiomethyl)-3-cephem-4-carboxylic acid
7-Amino-3-(4-methyl-1,2,3-triazol-5-ylthiomethyl)-3-cephem-4-carboxylic acid
7-Amino-3-(1,3,4-oxadiazol-2-ylthiomethyl)-3-cephem-4-carboxylic acid
7-Amino-3-(5-methyl-1,3,4-oxadiazol-2-ylthiomethyl)-3-cephem-4-carboxylic acid
7-Amino-3-(4-pyrimidylthiomethyl)-3-cephem-4-carboxylic acid
7-Amino-3-(2-pyrazinylthiomethyl)-3-cephem-4-carboxylic acid
7-Amino-3-(3-pyridylthiomethyl)-3-cephem-4-carboxylic acid
7-Amino-3-(4-pyridylthiomethyl)-3-cephem-4-carboxylic acid
7-Amino-3-(1-oxide-2-pyridylthiomethyl)-3-cephem-4-carboxylic acid.

EXAMPLE 7

α-t-Butoxycarbonylamino-m-ureidophenylacetic acid

A mixture of m-nitrophenylglycine (58.0 g, 0.296 mol), MgO (23.92 g, 0.6 mol) and t-butoxylcarbonyl azide (85.2 g, 0.6 mol) in 50% aqueous dioxane (700 ml) was heated at 45° for 17 hours. The reaction was cooled, water (750 ml) was added, and the mixture was filtered. The filtrate was washed with ether (1000 ml), acidified to pH 3 with 40% $H_3PO_4$, and extracted with ethyl acetate. The dried extracts were evaporated to give α-t-butoxycarbonylamino-m-nitrophenylacetic acid (70.3 g).

The above product (50.0 g, 0.17 mol) was dissolved in methanol (900 ml) and hydrogenated at 50 psi for 1 hour with 5% palladium on carbon (4 g). Evaporation of the filtered reaction solution gave the m-amino product (44.8 g).

A solution of α-t-butoxycarbonylamino-m-aminophenylacetic acid (2.66 g, 0.01 mol) and potassium cyanate (0.81 g, 0.01 mol) in a mixture of water (35 ml) and acetic acid (2.5 ml) was heated at 56° for 3 hours. The solution was cooled, acidified with 40% $H_3PO_4$, and extracted with ethyl acetate. The dried extracts were evaporated to give the title product: mp 93°–95° (dec).

EXAMPLE 8

D-α-t-Butoxycarbonylamino-p-(3-methylureido)-phenylacetic acid

Methyl isocyanate (0.314 g, 5.5 mmol) was added to a solution of α-t-butoxycarbonylamino-p-aminophenylacetic acid (1.35 g, 5 mmol) in acetone (100 ml). The reaction was stirred at room temperature for 1 hour. More methyl isocyanate (0.2 g) was added and the solution was stirred an additional 2 hours. The solvent was evaporated and the residue was dissolved in water containing enough $NaHCO_3$ to maintain pH 8. The basic solution was washed with ethyl acetate, acidified to pH 1.5 with 3N HCl, and extracted with ethyl acetate. The dried extracts were evaporated to give the title product.

EXAMPLE 9

D-α-t-Butoxycarbonylamino-p-(3,3-dimethylureido)-phenylacetic acid

Dimethylcarbamoyl chloride (1.07 g, 0.01 mol) is added slowly to a solution of D-α-t-butoxycarbonylamino-p-aminophenylacetic acid (2.66 g, 0.01 mol) in 50 ml of dioxane containing triethylamine (2.02 g, 0.02 mol). After stirring at room temperature for several hours the mixture is concentrated to half volume, diluted with water and the pH adjusted to 8. After extraction with ether the aqueous phase is adjusted to pH 2 and extracted with ethyl acetate. Evaporation of the dried ethyl acetate extracts in vacuo gave the desired product.

EXAMPLE 10

α-t-Butoxycarbonylamino-p-thioureidophenylacetic acid

To a suspension of α-acetamido-p-aminophenylacetic acid (1.04 g, 5 mmol) in water (5 ml) was added 10% NaOH until solution was effected. The solution was diluted with an equal volume of ethanol and then t-butyl isothiocyanate (1.64 g, 15 mmol) in ethanol was added. The reaction was stirred at room temperature overnight and then refluxed 24 hours. The ethanol was evaporated in vacuo and the aqueous phase was acidified and filtered. The aqueous filtrate was extracted with ethyl acetate. The dried extracts were evaporated to give α-acetamido-p-(3-t-butylthioureido)phenylacetic acid.

The above product (0.1 g, 0.31 mmol) was heated with 12N HCl (1 ml) on a steam bath for 15 minutes after gas evolution stopped. The solution was diluted with water and concentrated in vacuo. The residue was mixed with water and concentrated an additional three times and then triturated with isopropanol to give the title product.

EXAMPLE 11

3-(5-Methyl-1,3,4-thiadiazol-2-ylthiomethyl)-7-(α-amino-m-ureidophenylacetamido)-3-cephem-4-carboxylic acid To a solution of t-butyl 7-amino-3-(5-methyl-1,3,4-thiadiazol-2-ylthiomethyl)-3-cephem-4-carboxylate (1.2 g, 3 mmol) and α-t-butoxycarbonylamino-m-ureidophenylacetic acid (0.93 g, 3 mmol) in tetrahydrofuran (75 ml) was added dicyclohexylcarbodiimide (0.61 g, 3 mol). The mixture was stirred at room temperature for 3 hours and then the solid urea was filtered off. The filtrate was evaporated in vacuo and the residue was triturated with ether. The solid product was chromatographed on silica gel using 50:50 benzene: acetone as eluent.

The t-butyl ester (0.88 g) was stirred with trifluoroacetic acid (12 ml) for one hour at room temperature. The solution was evaporated in vacuo at a temperature below 30°. The residue was triturated with ether to give the trifluoroacetate salt of the title compound: 0.75 g, mp 158°–165° (dec). The zwitterionic product is obtained from the salt by standard methods such as described in Example 2.

EXAMPLE 12

3-(1,2,3-Triazol-4-ylthiomethyl)-7-(α-amino-m-ureidophenylacetamido)-3-cephem-4-carboxylic acid When 7-ACA, 4-mercapto-1,2,3-triazole, and α-t-butoxycarbonylamino-m-ureidophenylacetic acid are reacted according to the procedure of Example 5 the title compound is obtained.

EXAMPLE 13

3-(1-Methyltetrazol-5-ylthiomethyl)-7-(α-amino-m-ureidophenylacetamido)-3-cephem-4-carboxylic acid Using α-t-butoxycarbonylamino-m-ureidophenylacetic acid in the procedure of Example 4, the title compound was obtained: mp 158°–165° (trifluoroacetic acid salt).

EXAMPLE 14

3-Methyl-7-(α-amino-m-ureidophenylacetamido)-3-cephem-4-carboxylic acid

The title compound was prepared according to the procedure of Example 3 using α-t-butoxycarbonylamino-m-ureidophenylacetic acid and t-butyl 7-aminodesacetoxycephalosporanic acid.

EXAMPLE 15

When the 7-aminocephem compounds enumerated in Example 6 are acylated with α-t-butoxycarbonylamino-m-ureidophenylacetic acid and the amino group is subsequently deblocked according to the procedure of Example 2, the corresponding 7-(α-amino-m-ureidophenylacetamido)cephalosporin compound is obtained.

EXAMPLE 16

3-(1-Methyltetrazol-5-ylthiomethyl)-7-[α-amino-p-(3-methylureido)phenylacetamido]-3-cephem-4-carboxylic acid To a solution α-t-butoxycarbonylamino-p-(3-methylureido)phenylacetic acid (2.1 g, 6.5 mmol) in dry tetrahydrofuran (75 ml) was added triethylamine (0.89 ml) and N-methylmorpholine (3 drops) causing a solid to precipitate. The suspension was cooled to −10° and isobutyl chloroformate (0.84 ml) was added. The reaction was stirred at −10° for 45 minutes and then a solution of 7-amino-3-(1-methyltetrazol-5-ylthiomethyl)-3-cephem-4-carboxylic acid (2.13 g, 6.5 mmol) in a mixture of 50% aqueous tetrahydrofuran (25 ml) and triethylamine (0.89 ml) was added over a 15 minute period. The reaction was stirred at ice bath temperature for one hour and then at room temperature 1 hour. The organic solvents were evaporated and the residue was dissolved in water (150 ml). The aqueous phase was washed with ethyl acetate, adjusted to pH 2, and extracted with ethyl acetate (800 ml). The dried extracts were concentrated to a volume of 100 ml and the N-protected product was collected, 1.63 g.

The above product (1.2 g) was added to ice cold trifluoracetic acid (10 ml) and stirred with cooling for 8 minutes. The solution was partially evaporated and then diluted with ether. The trifluoroacetate salt was collected. The salt was dissolved in water (100 ml) and treated with basic ion-exchange resin (Amberlite IR-45) until pH 5.4 was obtained. After filtration the aqueous solution was lypholized to give the title product (0.44 g).

EXAMPLE 17

Acylation of 7-ADCA, 7-amino-3-(5-methyl-1,3,4-thiadiazol-2-ylthiomethyl)-3-cephem-4-carboxylic acid or any of the cephem compounds named in Example 6 with α-t-butoxycarboxyamino-p-(3-methylureido)-phenylacetic acid followed by deblocking according to the procedure of Example 2 gives the corresponding 7-[α-amino-p-(3-methylureido)-phenylacetamido]-cephem compound. 7-[α-amino-p-(3-methylureido)phenylacetamido]-3-(1,2,3-triazol-4-ylthiomethyl)-3-cephem-4-carboxylic acid is prepared by reacting 7-ACA with α-t-butoxycarbonylamino-p-(3-methylureido)phenylacetic acid and then with 4-mercapto-1,2,3-triazole with subsequent deblocking of the amino grouping according to the procedure of Example 5.

EXAMPLE 18

Using α-t-butoxycarbonylamino-p-(3,3-dimethylureido) phenylacetic acid to acylate the 7-aminocephem compounds of Examples 2,3,4 and 6 according to the procedure of Example 2 gives the appropriate 7-[α-amino-p-(3,3-dimethylureido)-phenylacetamido]cephalosporanic acids. Using N-t-butoxycarbonyl-p-(3,3-dimethylureido)phenylglycine as the acylating agent in the procedure of Example 5 gives 7-[α-amino-p-(3,3-dimethylureido)-phenylacetamido]-3-(1,2,3-triazol-4-ylthiomethyl)-3-cephem-4-carboxylic acid as the product.

EXAMPLE 19

When 7-amino-3-(5-methyl-1,3,4-thiadiazol-2-ylthiomethyl)-3-cephem-4-carboxylic acid is reacted with α-t-butoxycarbonylamino-p-thioureidophenylacetic acid according to the procedure of Example 2, 3-(5-methyl-1,3,4-thiadiazol-2-ylthiomethyl)-7-(α-amino-p-thioureidophenylacetamido)-3-cephem-4-carboxylic acid is obtained.

EXAMPLE 20

When 7-ACA, α-t-butoxycarbonylamino-p-thioureidophenylacetic acid, and 4-mercapto-1,2,3-triazole are reacted by the procedure of Example 5, 3-(1,2,3-triazole-4-ylthiomethyl)-7-(α-amino-p-thioureidophenylacetamido)-3-cephem-4-carboxylic acid is obtained.

EXAMPLE 21

When α-t-butoxycarbonylamino-p-thioureidophenylacetic acid is used to acylate any of the 7-aminocephem compounds listed in Examples 3,4, and 6, the corresponding 7-(α-amino-p-thioureidophenylacetamido)cephalosporanic acids are obtained.

EXAMPLE 22

α-t-Butoxycarbonylamino-p-methylaminophenylacetic acid

Method A

A mixture of α-t-butoxycarbonylamino-p-aminophenylacetic acid (26.6 g, 0.1 mol), formaldehyde (8.1 ml of a 37% aq. solution) and phthalimide (14.7 g, 0.1 mol) in 200 ml of absolute ethanol is heated at reflux for 1 hour. After cooling to room temperature Raney nickel catalyst is added and the mixture is hydrogenated under 60 psi of $H_2$ at 100° for 2 hours. The catalyst is filtered off and the solvent is evaporated in vacuo. Following chromatography on silica gel the desired prouct is obtained.

Method B

Dimethylsulfate (1.26 g, 0.01 mol) is added gradually to a solution of α-t-butoxycarbonylamino-p-aminophenylacetic acid (13.3 g, 0.05 mol) in 50 ml of 50% aqueous methanol containing NaOH (2.4 g, 0.06 mol). When the reaction was complete the reaction mixture was acidified and extracted with ethyl acetate. The desired product was isolated by column chromatography on silica gel.

EXAMPLE 23

α-t-Butoxycarbonylamino-p-(1-methylureido)phenylacetic acid

α-t-Butoxycarbonylamino-p-methylaminophenylacetic acid is reacted with potassium cyanate according to the procedure in Example 1 to give the title compound.

EXAMPLE 24

3-(1,2,3-Triazol-4-ylthiomethyl)-7-[α-amino-p-(1-methylureido)phenylacetamido]-3-cephem-4-carboxylic acid When α-t-butoxycarbonylamino-p-(1-methylureido)-phenylacetic acid is reacted with 7-ACA and 4-mercapto-1,2,3-triazole according to the procedure of Example 5, the title compound is obtained.

EXAMPLE 25

Acylation of any of the 7-aminocephem compounds enumerated in Examples 2,3,4 or 6 with α-t-butoxycarbonylamino-p-(1-methylureido)phenylacetic acid according to the procedure of Example 2 gives the appropriate 7-[α-amino-p-(1-methylureido)-phenylacetamido]-3-cephem compound.

EXAMPLE 26

When 7-ACA is acylated with α-t-butoxycarbonylamino-p-(3-methylureido)phenylacetic acid or α-t-butoxycarbonylamino-p-(3,3-dimethylureidophenylacetic acid and the product treated with 4-mercapto-1,2,3-triazole, all according to the procedure of Example 5, the corresponding 3-(1,2,3-triazol-4-ylthiomethyl)-7-(p-substitutedureidophenylacetamido)-3-cephem-4-carboxylic acid is obtained.

EXAMPLE 27

When the N-t-butoxycarbonyl derivative of 7-(α-amino-p-ureidophenylacetamido)cephalosporanic acid from Example 5 was deblocked according to the procedure in Example 2, 7-(α-amino-p-ureidophenylacetamido)cephalosporanic acid was obtained.

When 7-ACA was acylated with α-t-butoxycarbonylamino-m-ureidophenylacetic acid according to the procedure of Example 5 and then deblocked 7-(α-amino-p-ureidophenylacetamido)cephalosporanic acid was obtained.

EXAMPLE 28

Following the procedure of Example 2, 7-ACA is reacted with the N-t-butoxycarbonyl derivatives of α-amino-p-(3-methylureido)phenylacetic acid, α-amino-p-(3,3-dimethylureido)phenylacetic acid, α-amino-p-(1-methylureido)phenylacetic acid, or α-amino-p-thioureidophenylacetic acid to give the corresponding 7-(α-amino-p-substituted ureidophenylacetamido)cephalosporanic acid.

EXAMPLE 29

Acylation of 7-amino-3-methylthiomethyl-3-cephem-4-carboxylic acid according to the procedure of Example 2 with the N-protected derivative of α-amino-p-ureidophenylacetic acid, α-amino-m-ureidophenylacetic acid, α-amino-p-(3-methylureido)phenylacetic acid, α-amino-p-(3,3-dimethylureido)phenylacetic acid, α-amino-p-(1-methylureido)phenylacetic acid, or α-amino-p-thioureidophenylacetic acid gives the corresponding 7-(α-amino-α-ureidophenylacetamido)-3-methylthiomethyl-3-cephem-4-carboxylic acid.

EXAMPLE 30

When 7-amino-3-methoxymethyl-3-cephem-4-carboxylic acid is acylated by the procedure of Example 2 with the acetic acid compounds listed in Example 29 the corresponding 7-(α-amino-α-ureidophenylacetamido)-3-methoxymethyl-3-cephem-4-carboxylic acid is obtained.

EXAMPLE 31

An injectable pharmaceutical composition is prepared by dissolving 500 mg of sodium 3-(5-methyl-1,3,4-thiadiazol-2-ylthiomethyl)-7-(α-amino-p-ureidophenylacetamido)-3-cephem-4-carboxylate in sterile water or sterile normal saline solution (1–2 ml). Other cephalosporins of this invention are formulated in a similar manner.

An antibacterial capsule is comprised of the following components:

| | |
|---|---|
| cephalosporin | 500 mg |
| lactose | 250 mg |
| magnesium stearate | 75 mg |

What is claimed is:
1. A compound of the formula

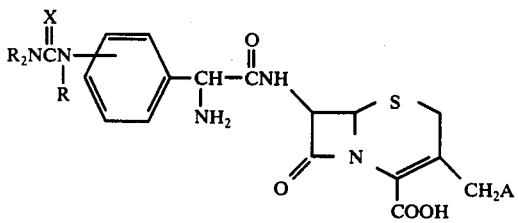

wherein:
the $R_2NCXNR$ group is at the para or meta position;
R is hydrogen or lower alkyl of 1–4 carbon atoms;
X is oxygen or sulfur; and
A is hydrogen, or acetoxy;
or a non-toxic pharmaceutically acceptable salt thereof.

2. A compound as claimed in claim 1 where the $R_2NCXNR$ group is at the meta position.

3. A compound as claimed in claim 1 where the $R_2NCXNR$ group is at the para position.

4. A compound as claimed in claim 3 where X is oxygen.

5. A compound as claimed in claim 4 being the compound 3-methyl-7-(α-amino-p-ureidophenylacetamido)-3-cephem-4-carboxylic acid.

6. A compound as claimed in claim 2 being the compound 3-methyl-7-(α-amino-m-ureidophenylacetamido)-3-cephem-4-carboxylic acid.

7. A compound as claimed in claim 1 where X is sulfur.

8. A compound as claimed in claim 7 where R is hydrogen.

9. A compound as claimed in claim 4 where each R is hydrogen or methyl.

10. A compound as claimed in claim 9 being the compound 3-acetoxymethyl-7-(α-amino-p-ureidophenylacetamido)-3-cephem-4-carboxylic acid.

11. A compound as claimed in claim 2 where X is oxygen and each R is hydrogen or methyl.

12. A compound as claimed in claim 11 being the compound 3-acetoxymethyl-7-(α-amino-m-ureidophenylacetamido)-3-cephem-4-carboxylic acid.

13. A compound as claimed in claim 8 being the compound 3-methyl-7-(α-amino-p-thioureidophenylacetamido)-3-cephem-4-carboxylic acid.

14. A compound as claimed in claim 8 being the compound 3-acetoxymethyl-7-(α-amino-p-thioureidophenylacetamido)-3-cephem-4-carboxylic acid.

15. An antibacterially effective pharmaceutical composition comprising a compound as claimed in claim 1 and a pharmaceutically acceptable carrier therefore.

* * * * *